US009023056B2

(12) United States Patent
Berberich

(10) Patent No.: US 9,023,056 B2
(45) Date of Patent: May 5, 2015

(54) APPARATUS FOR TARGETING AND FORMING DRILL CHANNELS IN THE TIBIA

(75) Inventor: Sascha Berberich, Tuttlingen (DE)

(73) Assignee: Karl Storz GmbH & Co., KG (DE)

( * ) Notice: Subject to any disclaimer, the term of this patent is extended or adjusted under 35 U.S.C. 154(b) by 44 days.

(21) Appl. No.: 13/536,198

(22) Filed: Jun. 28, 2012

(65) Prior Publication Data

US 2013/0006254 A1    Jan. 3, 2013

(30) Foreign Application Priority Data

Jun. 28, 2011    (DE) .......................... 10 2011 106 729

(51) Int. Cl.
*A61B 17/17*    (2006.01)

(52) U.S. Cl.
CPC ......... *A61B 17/1714* (2013.01); *A61B 17/1764* (2013.01)

(58) Field of Classification Search
USPC ................................ 606/86 R, 87–88, 96–98
See application file for complete search history.

(56) References Cited

U.S. PATENT DOCUMENTS

| 5,968,050 | A | 10/1999 | Torrie |
| 7,695,479 | B1 * | 4/2010 | Metzger ........................ 606/102 |

| 2003/0216742 | A1 | 11/2003 | Wetzler et al. |
| 2009/0143784 | A1 * | 6/2009 | Petersen et al. ................. 606/96 |
| 2010/0114184 | A1 * | 5/2010 | Degtyar et al. ............. 606/86 R |

FOREIGN PATENT DOCUMENTS

| DE | 102006062382 A1 | 6/2008 |
| DE | 102007057075 A1 | 5/2009 |

OTHER PUBLICATIONS

German Search Report; Application No. DE 10 2011 106 729.2; Issued: Jan. 24, 2012; 5 pages.

* cited by examiner

*Primary Examiner* — Nicholas Woodall
*Assistant Examiner* — Larry E Waggle, Jr.
(74) *Attorney, Agent, or Firm* — St. Onge Steward Johnston & Reens LLC

(57) ABSTRACT

An apparatus for targeting and forming drill channels in the tibia in the area of a knee joint during reconstruction of an anterior cruciate ligament, having a handle, which includes a drill sleeve for configuring a first target point on the tibia and an arm extending beyond the distal end of the drill sleeve for determining a second target point on the tibial plateau. To provide an apparatus for targeting and forming drill channels in the tibia that is adaptable to the patient's individual anatomical idiosyncrasies, it is proposed that at least one portion of the arm should be configured as elastically reshapable.

6 Claims, 1 Drawing Sheet

APPARATUS FOR TARGETING AND FORMING DRILL CHANNELS IN THE TIBIA

CROSS-REFERENCE TO RELATED APPLICATIONS

The present application claims priority of German patent application No. 10 2011 106 729.2 filed on Jun. 28, 2011, the content of which is incorporated herein by reference.

FIELD OF THE INVENTION

The invention relates to an apparatus for targeting and forming drill channels in the tibia in the area of a knee joint during reconstruction of an anterior cruciate ligament, having a handle, which comprises a drill sleeve for configuring a first target point on the tibia and an arm extending beyond the distal end of the drill sleeve for determining a second target point on the tibial plateau.

BACKGROUND OF THE INVENTION

A generic tibial target apparatus is known, for example, from DE 10 2007 057 075 A1.

The anterior cruciate ligament, which extends from the upper plateau (tibial plateau) of the tibia to the inside of the lower end of the femur, constitutes together with the posterior tibial ligament the two most important ligaments that hold the knee joint.

Because of this important holding function of the anterior cruciate ligament, in the event of a tearing of the anterior cruciate ligament it is necessary to reconstruct the anterior cruciate ligament by a natural tendon or by a tendon implant. For this purpose a borehole is made in the bone from the outside of the tibia, said borehole emerging at the height of the tibia The borehole is then continued through the femur until it emerges on the femur's outside. Then the tendon implant or the replacement ligament is inserted into both boreholes and secured in such a way that said replacement ligament can assume the function of the natural anterior cruciate ligament.

For successful reconstruction of the anterior cruciate ligament, it is decisive that the drill channel created from the outside of the tibia to the tibial plateau stands in an anatomic alignment that approximates as closely as possible the alignment of the natural cruciate ligament in a particular knee position.

However, because the tibial plateau has individualized anatomical features for every patient, particular requirements are posed in configuring the closest possible anatomical alignment of the drill channel and thus as well in the objectives for aligning the drill channel.

SUMMARY OF THE INVENTION

It is consequently the object of the invention to provide an apparatus of the aforementioned type that can be adapted to the patient's individual anatomic idiosyncrasies.

This object is achieved according to the invention in a manner marked by the features of patent claim 1. At least a portion of the arm is thereby configured so that it can be elastically reshaped.

Advantageous refinements of the invention are the subject matter of the dependent claims.

Owing to the elastic reshapable property of at least one portion of the arm, it is possible for the first time to adjust the support angle of the distal end of the arm to the respective individual anatomical configuration of the patient's tibia plateau to determine the target point on the tibia plateau. However, despite the individual adaptability, to maintain the targeted exactitude of the inventive tibial target device, the arm of the handle is not configured as reshapable in its entirety but rather only in partial areas.

According to a practical embodiment of the invention, it is proposed that the partial area of the arm should be configured as reversibly reshapable in order to be able to use the inventive tibial target device for further individual adaptations.

With a preferred embodiment for configuring the reversibly elastically reshapable portion of the arm, it is proposed according to the invention that the at least one portion should consist of a shape memory alloy. Shape memory alloys, also known as memory metals, have the property that they after being reshaped they almost recall their original shape and can be transferred back into their starting form because of a temperature-dependent lattice transformation.

This temperature-controlled reversal of the reshaping can occur, for example, after the operation during the thermal sterilization of the tibial target device.

Finally it is proposed with the invention that the shape memory alloy is a NiTi alloy, in particular Nitinol.

To ensure that, despite the individual adjustment of the second target point to the height of the tibial plateau, no strong or relevant lateral displacement results, it is further proposed with the invention that the arm should comprise in the proximal end area a vertical portion running essentially parallel to the handle and that the at least one reshapable portion of the arm should be positioned in this vertical portion.

Additional properties and advantages of the invention can be seen from the related drawings, in which an embodiment of an inventive apparatus for targeting and forming drill channels in the tibia is shown only by way of example, without restricting the invention to this embodiment. The drawings are as follows.

DETAILED DESCRIPTION OF THE INVENTION

Figure 1:
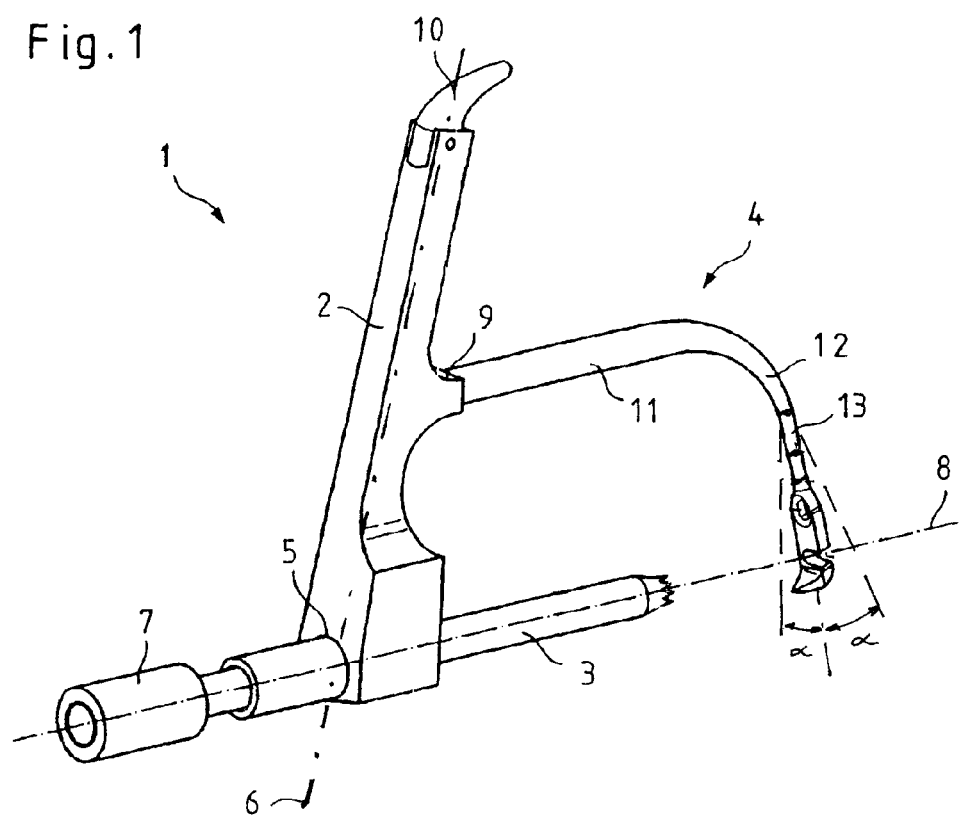
FIG. 1 shows a perspective view of an inventive apparatus for targeting and forming drill channels in the tibia.

FIG. 1 shows an apparatus 1 for targeting and forming drill channels in the tibia. This tibial targeting apparatus 1 consists of a rod-shaped handle 2 on which two targeting aids are detachably mounted, namely a drill sleeve 3 and an arm 4.

The drill sleeve 3 is mounted on a free end of the handle 2 in such a way that, mounted in a borehole 5 of the handle 2, it extends essentially diagonally to the longitudinal axis 6 of the handle 2. The clamping sleeve 7 can be detached and reattached again in its mounting in the handle 2 in such a way that the drill sleeve 3 can slide back and forth in the direction of its longitudinal axis 8 and also can be completely removed from the borehole 5 of the handle 2.

The arm 4 that forms the second targeting aid branches off in the illustrated embodiment at approximately medium height from the rod-shaped handle 2. On the handle 2 the arm 4 is mounted in a recess 9 in which the arm 4 can be fastened via a clamping lever 10 mounted on the free end of the handle 2 that is opposite the drill sleeve 3.

As an alternative to the illustrated configuration of the recess 9 for mounting the arm 4, it is also possible of course to secure the arm 4 on the handle 2 by another bracket or even to configure the arm 4 as a single piece with the handle 2.

The arm 4 comprises a horizontal portion 11 running essentially parallel to the drill sleeve 3 and mounted on the handle 2 and a vertical portion 12 that connects distally on it and extends in the direction of the drill sleeve 3, such that the free end of the vertical portion 12 extends beyond the distal end of the drill sleeve 3 in the direction of the longitudinal axis 8 and is positioned approximately at the height of the longitudinal axis 8. The vertical portion 12 forms the distal end section of the arm 4 and runs essentially parallel to the handle 2.

As can further be seen from FIG. 1, the vertical portion 12 of the arm 4 comprises a portion 13 that, made of a shape memory alloy, can be reversibly elastically reshaped. Possible divergent angles alpha in the distal and proximal directions are indicated in broken lines in FIG. 1. This arrangement of the portion 13 ensures that the individual adaptation has an influence essentially only on the height of the tibial plateau without causing a strong or relevant lateral displacement.

Alternatively to using only one reshapable portion 13, it is also possible, however, to configure several portions 13 of the arm 4 as elastically reshapable.

Shape memory alloys, or alloys called memory metals, have the characteristic that after a reshaping they seem to recall their original shape and can be converted back into their original shape by means of a temperature-dependent lattice transformation.

This temperature-controlled replacement of the reshaped portion 13 of the arm 4 can occur, for example, after the operation during the thermal sterilization of the target apparatus 1. A preferred material for configuring a shape memory alloy of this type is one of the NiTi alloys, in particular Nitinol.

Figure 2:
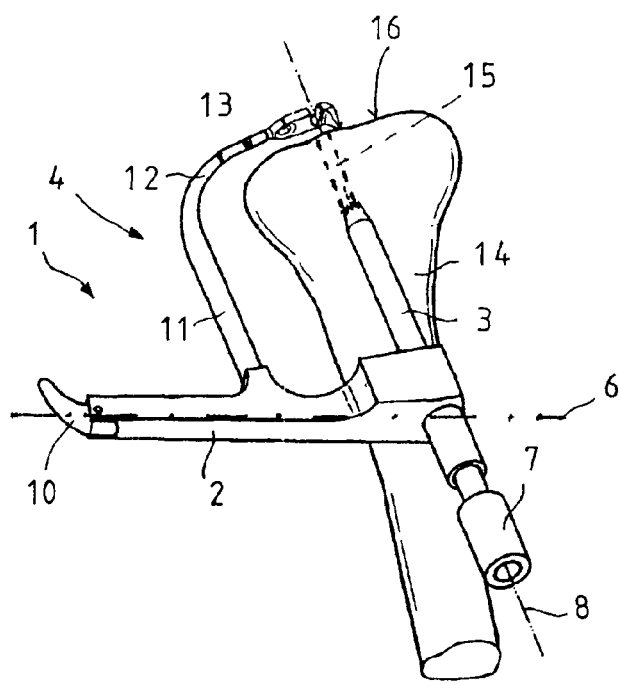
FIG. 2 shows the use of the apparatus from FIG. 1 in configuring a first tibial drill channel.

FIG. 2 shows the target apparatus 1 in a position applied to the tibia 14 for configuring a first drill channel 15. The distal end of the drill sleeve 3 marks a first target point on the outside of the tibia 14, which is situated closely below the widening of the tibia 14.

The distal end of the arm 4 is situated on the tibial plateau 16 and constitutes the second target point, which simultaneously forms the exit point of the drill channel 15.

Because the tibial plateau 16 comprises anatomical idiosyncrasies for each patient, it is advantageous in configuring the most anatomically exact alignment of the drill channel 15 that at least one portion 13 of the arm 4 should be elastically reshapably configured in order to be able to adapt the support angle of the distal end of the arm 4 to the particular individual anatomical configuration of the patient's tibial plateau 16 to determine the target point on the tibial plateau 16. However, in order to preserve the target precision of the tibial target apparatus 1 despite the individual adaptability, the arm 4 of the handle 2 is not configured as reshapable in its entirety, but only in portions.

A tibial target apparatus configured in this manner is distinguished in that it is both simple to operate and adaptable to the patient's individual anatomical idiosyncrasies.

What is claimed is:

1. An apparatus for targeting and forming drill channels in the tibia in the area of a knee joint during reconstruction of an anterior cruciate ligament, having a handle, which comprises a drill sleeve for configuring a first target point on the tibia and an arm extending beyond a distal end of the drill sleeve for determining a second target point on the tibial plateau,
    wherein
        exclusively one position-specific portion of the arm is configured as elastically reshapable for adjusting a support angle of a distal end of the arm to the respective individual anatomical configuration of the tibial plateau and wherein the arm in a distal end portion comprises a vertical portion running essentially parallel to the handle and that said reshapable portion of the arm is positioned in this vertical portion and is configured only as a portion of this vertical portion.

2. The apparatus according to claim 1, wherein the reshapable portion of the arm is configured as reversibly reshapable.

3. The apparatus according to claim 2, wherein the at least one reshapable portion of the arm consists of a shape memory alloy.

4. The apparatus according to claim 1, wherein the at least one reshapable portion of the arm consists of a shape memory alloy.

5. The apparatus according to claim 4, wherein the shape memory alloy is a NiTi-alloy.

6. The apparatus according to claim 5, wherein the NiTi-alloy is Nitinol.

* * * * *